US010428115B2

(12) United States Patent
Lee et al.

(10) Patent No.: US 10,428,115 B2
(45) Date of Patent: Oct. 1, 2019

(54) DYNORPHIN A ANALOGS WITH BRADYKININ RECEPTORS SPECIFICITY FOR MODULATION OF NEUROPATHIC PAIN

(71) Applicant: THE ARIZONA BOARD OF REGENTS ON BEHALF OF THE UNIVERSITY OF ARIZONA, Tucson, AZ (US)

(72) Inventors: Yeon Sun Lee, Tucson, AZ (US); Victor J. Hruby, Tucson, AZ (US); Frank Porreca, Tucson, AZ (US); Josephine Lai, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 14/893,800

(22) PCT Filed: May 23, 2014

(86) PCT No.: PCT/US2014/039431
§ 371 (c)(1),
(2) Date: Nov. 24, 2015

(87) PCT Pub. No.: WO2014/190313
PCT Pub. Date: Nov. 27, 2014

(65) Prior Publication Data
US 2016/0108090 A1    Apr. 21, 2016

Related U.S. Application Data

(60) Provisional application No. 61/827,497, filed on May 24, 2013, provisional application No. 61/835,463, filed on Jun. 14, 2013.

(51) Int. Cl.
| | |
|---|---|
| *A61K 38/04* | (2006.01) |
| *C07K 7/64* | (2006.01) |
| *C07K 7/08* | (2006.01) |
| *A61P 43/00* | (2006.01) |
| *C07K 14/665* | (2006.01) |
| *A61K 38/00* | (2006.01) |

(52) U.S. Cl.
CPC .............. *C07K 7/64* (2013.01); *C07K 7/08* (2013.01); *C07K 14/665* (2013.01); *A61K 38/00* (2013.01)

(58) Field of Classification Search
CPC ........ A61K 38/00; C07K 14/665; C07K 7/08; C07K 7/64
See application file for complete search history.

(56) References Cited

U.S. PATENT DOCUMENTS

| | | | |
|---|---|---|---|
| 4,396,606 A | 8/1983 | Goldstein | 424/177 |
| 4,462,941 A | 7/1984 | Lee et al. | 260/112.5 R |
| 4,518,711 A | 5/1985 | Hruby et al. | 514/11 |
| 5,006,510 A | 4/1991 | Ellis | 514/16 |

FOREIGN PATENT DOCUMENTS

| | | | | |
|---|---|---|---|---|
| WO | WO9325217 | 12/1993 | | A61K 37/00 |
| WO | WO9606626 | 3/1996 | | A61K 38/00 |
| WO | WO2009049233 | 4/2009 | | A61K 31/485 |

OTHER PUBLICATIONS

Lee et al, Amphipathic Non-opioid Dynorphin A Analogs to Inhibit Neuroexcitatory Effects at Central Bradykinin Receptors, Proceedings of the 24th American Peptide Symposium, 2015, pp. 1-2.*
Peake, Design and Synthesis of Dynorphin A Analogues for the Modulation of Chronic Pain, May 2011, pp. 1-16, from The University of Arizona.*
Wakimasu et al, Use of the 4-Methoxy-2,6-dimethylbenzenesulfonyl (Mds) Group to Synthesize Dynorphin [1-13] and Related Peptides, Chem. Pharm. Bull., 1981, 29, pp. 2592-2597.*
Water, from http://www.biology-online.org/dictionary/Water, pp. 1-3, accessed Apr. 24, 2014.*
Marley et al, Effects of Opioid Peptides Containing the Sequence of Met5-Enkephalin or Leu5-Enkephalin on Nicotine-Induced Secretion from Bovine Adrenal Chromaffin Cells, Journal of Neurochemistry, 1986, 46, pp. 1-11.*
Blast result for SEQ ID No. 30, from https://blast.ncbi.nlm.nih.gov/Blast.cgi#597967641, pp. 1-8, accessed Apr. 16, 2018.*
Blast result for SEQ ID No. 36, from https://blast.ncbi.nlm.nih.gov/Blast.cgi, pp. 1-6, accessed Apr. 16, 2018.*
Blast result for SEQ ID No. 43, from https://blast.ncbi.nlm.nih.gov/Blast.cgi, pp. 1-6, accessed Apr. 16, 2018.*
Blast result for SEQ ID No. 44, from https://blast.ncbi.nlm.nih.gov/Blast.cgi, pp. 1-6, accessed Apr. 16, 2018.*
Blast result for SEQ ID No. 45, from https://blast.ncbi.nlm.nih.gov/Blast.cgi, pp. 1-6, accessed Apr. 16, 2018.*
Blast result for SEQ ID No. 6, from https://blast.ncbi.nlm.nih.gov/Blast.cgi, pp. 1-6, accessed Apr. 17, 2018.*
International Search Report issued in application No. PCT/US2014/039431, dated Sep. 12, 2014 (10 pgs).
International Preliminary Report on Patentability issued in application No. PCT/US2014/039431, dated Dec. 3, 2015 (14 pgs).
Balvinder et al., "A Novel N-Terminal Cyclic Dynorphin A Analogue $^{cycloN.5}$[Trp$^3$, Trp$^4$, Glu$^5$] Dynorphin A-(1-11)NH$_2$ That Lacks the Basic N-Terminus," Journal of Medicinal Chemistry, vol. 46, No. 8, Apr. 10, 2003 (4 pgs).

(Continued)

*Primary Examiner* — Karlheinz R. Skowronek
*Assistant Examiner* — Li N Komatsu
(74) *Attorney, Agent, or Firm* — Don D. Cha; HDC IP Law, LLP

(57) ABSTRACT

Described are Dynorphin A analog compounds and uses thereof for treating pain in humans and lower animals by administering to a human or lower animal in need of treatment. The compounds interact with the bradykinin receptor to relieve pain. Preferred compounds are amphipathic [Des-Arg$^7$]-dynorphin A peptide analogs and specific cyclic dynorphin A peptide analogs.

8 Claims, 7 Drawing Sheets
Specification includes a Sequence Listing.

(56) References Cited

OTHER PUBLICATIONS

Berge et al., "Pharmaceutical Salts," Journal of Pharmaceutical Sciences, Jan. 1977, vol. 66, No. 1 (19 pgs).
Danelev et al., "Design, synthesis and anticoagulant studies of new antistasin isoform 2 and 3 amide analogues," Bulgarian Chemical Communications, vol. 41, No. 2, pp. 99-103, 2009 (6 pgs).
Faridian et al., "Inhibition of neuropathic pain via dynorphin analog LYS 1044," The FASEB Journal, 2012, vol. 26, abstract only (1 pg).
Krust et al., "Targeting surface nucleolin with multivalent HB-19 and related Nucant pseudopeptides results in distinct inhibitory mechanisms depending on the malignant tumor cell type," BMC Cancer, 2011, vol. 11, No. 333 (22 pgs).
Lai et al., "Dynorphin A activates bradykinin receptors to maintain neuropathic pain," Nature Neuroscience, vol. 9, No. 12, Dec. 2006 (7 pgs).
Lai et al., "Pronociceptive actions of dynorphin via bradykinin receptors," Neuroscience Letters, vol. 437, 2008, pp. 175-179 (5 pgs).
Lee et al., [Des-Arg$^7$]-Dynorphin A Analogs for Bradykinin-2 Receptor, Peptides Across the Pacific, Proceedings of the Twenty-Third American and the Sixth International Peptide Symposium, Jun. 22-27, 2013, vol. 23, May 1, 2013-Jun. 22, 2013, pp. 134-135 (4 pgs).
Lee et al., "Discovery of Amphipathic Dynorphin A Analogues to Inhibit the Neuroexcitatory Effects of Dynorphin A through Bradykinin Receptors in the Spinal Cord," Journal of the American Chemical Society, 2014, vol. 136, pp. 6608-6616 (9 pgs).
Lung et al., "Development of highly potent and selective dynorphin A analogues as new medicines," J. Peptide Res., 2005, vol. 66, pp. 263-276 (14 pgs).

* cited by examiner

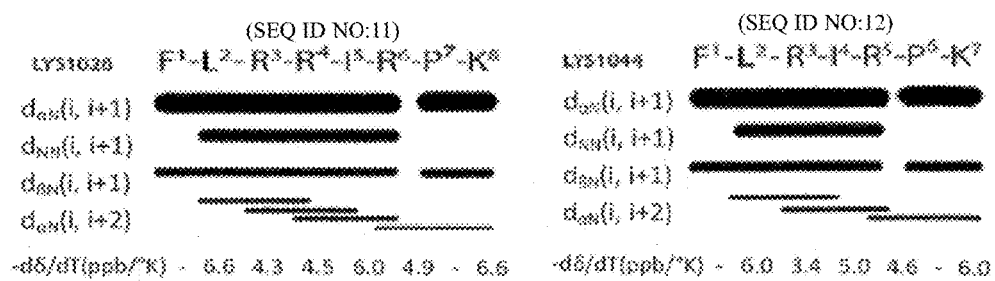
Figure 1 NOE Summary and Temperature Coefficient Values for LYS1026 and LYS1044
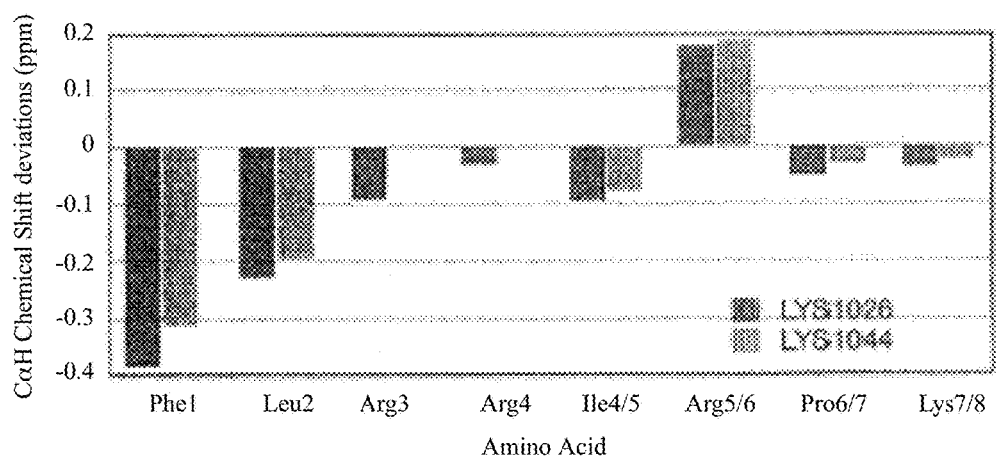
Figure 2 Chemical shift deviation of observed $C^{13}$ proton values from random coil values Figures 3A and 3B. Lowest energy structure and overlay of ten low energy structures of LYS1026(A) and LYS1044(B) from the simulated annealing molecule dynamics calculations

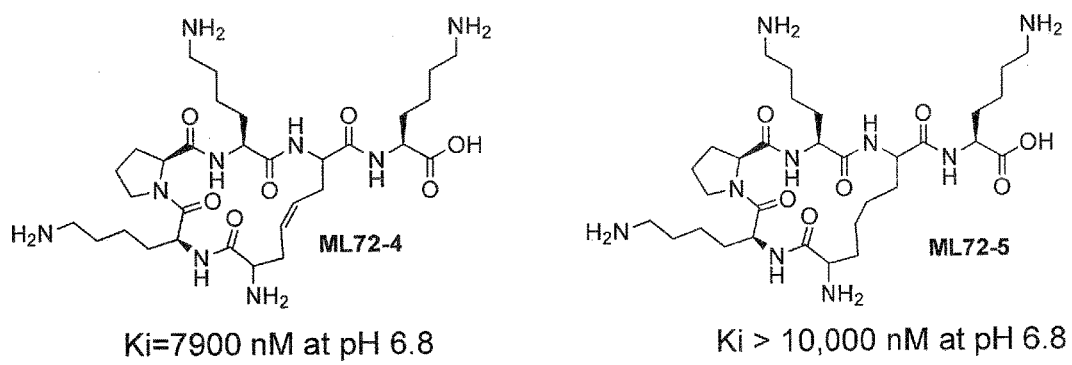
FIG. 4 Cyclic analogs and the binding affinities

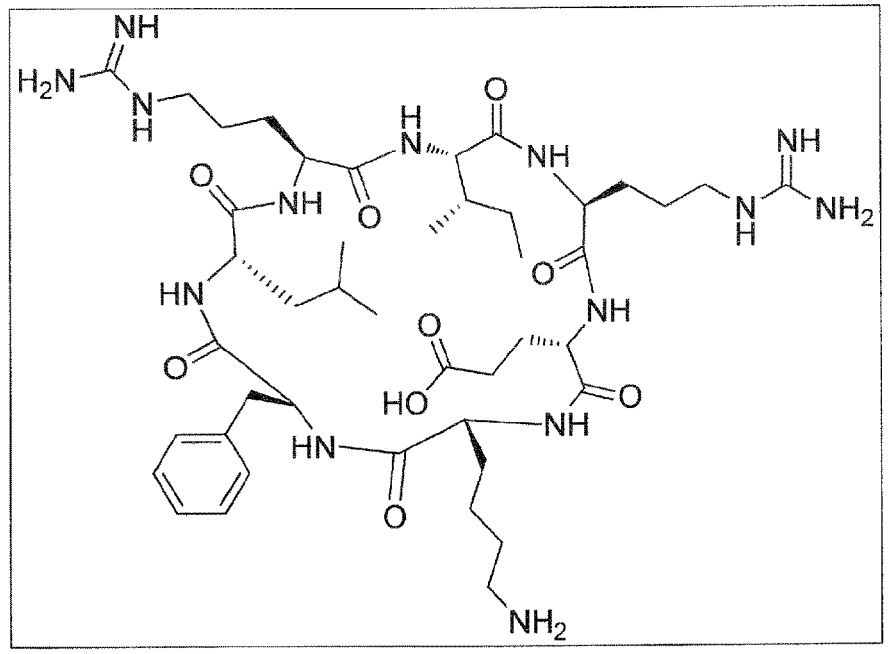
FIG. 5 Cyclic dynorphin A analogs retaining amphiphaticity
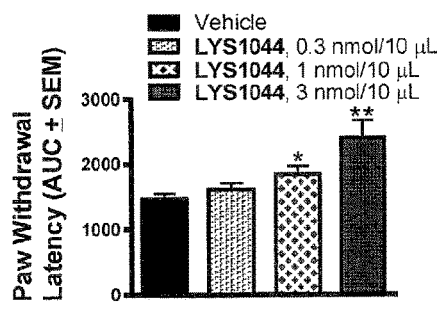
FIG. 6A
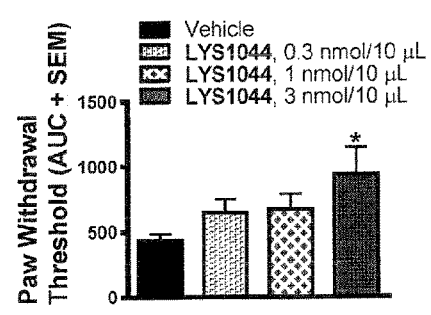
FIG. 6B
Figures 6A and 6B: Dose-dependent reversal of thermal hyperalgesia (left and tactile hypersensitivity (right) using varying doses of LYS1044 in SNL rats

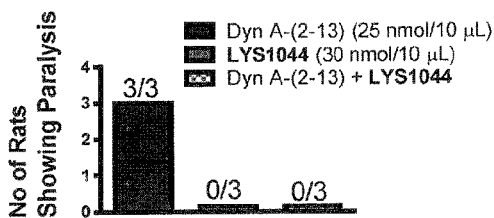
FIG. 7 Hindlimb (right) tests by i.th. administration of Dynorphin A-(2-13) or/and LYS1044 in naïve rats
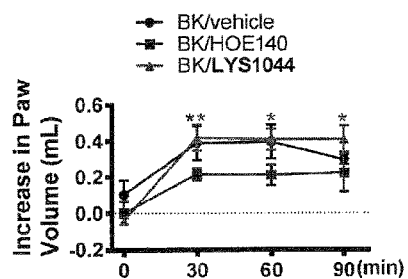
FIG. 8A
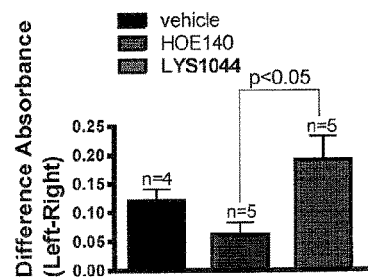
FIG. 8B
Figures 8A and 8B: Bradykinin-induced Plasma Extravasation or Changes in Paw Volume
FIG. 9 Wang (left) & Rink Amide Resin (right)

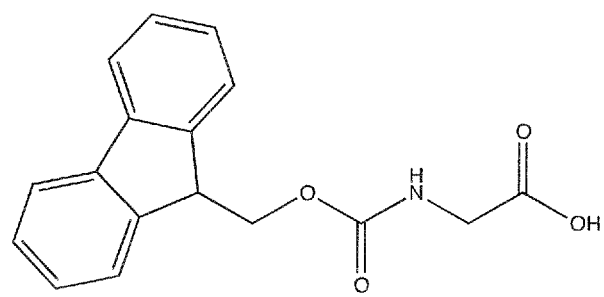
FIG. 10. Fmoc-Gly-OH
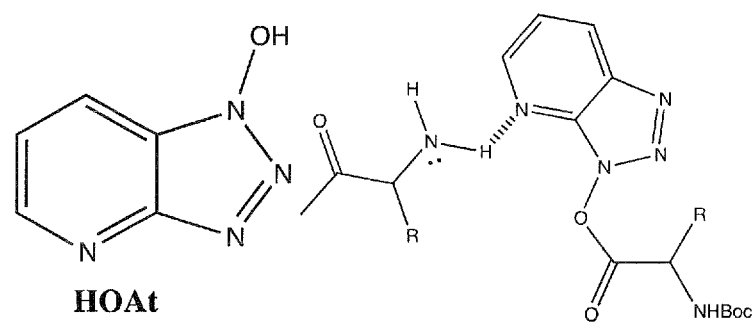
FIG. 11 HOAt and the Neighboring Group Effect

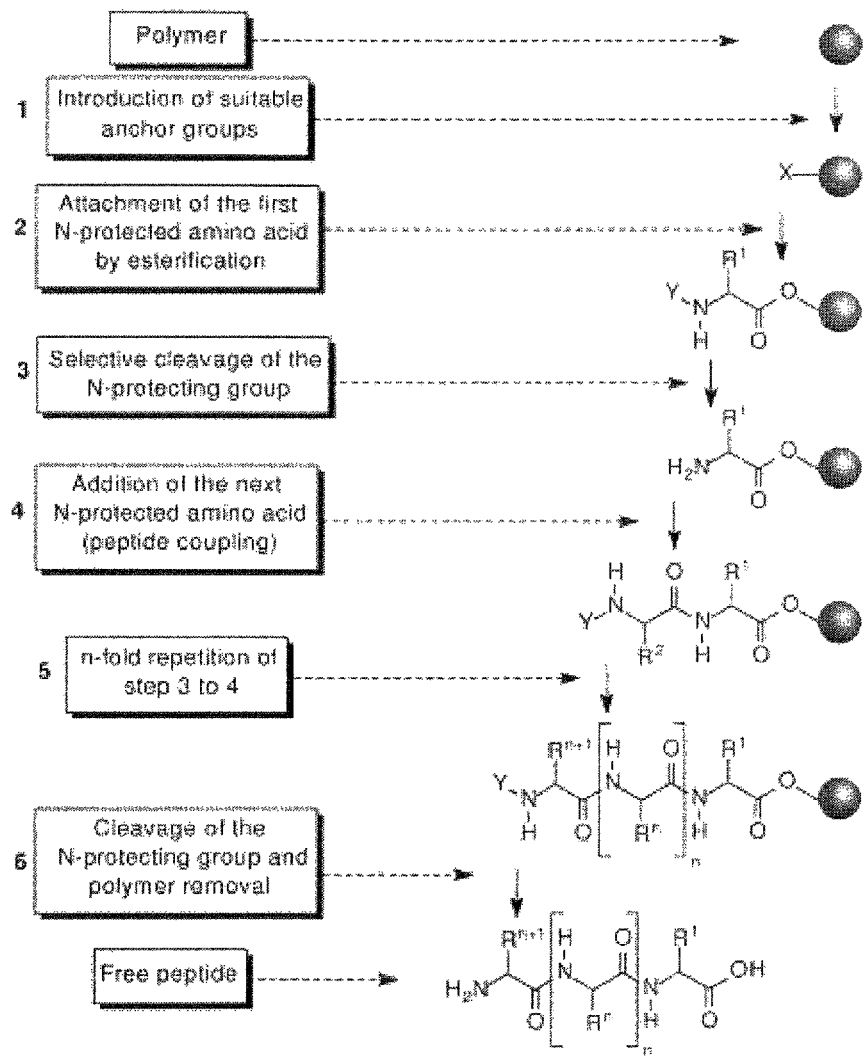
FIG. 12. General Scheme for Solid Phase Peptide Synthesis

DYNORPHIN A ANALOGS WITH BRADYKININ RECEPTORS SPECIFICITY FOR MODULATION OF NEUROPATHIC PAIN

STATEMENT REGARDING FEDERALLY FUNDED RESEARCH

This invention was made with Government support under Grant No. P01 DA006284, awarded by the National Institutes of Health (NIH). The Government has certain rights in the invention.

FIELD OF THE INVENTION

The present invention relates to pain management, and more particularly to compounds for relieving pain without the usual side effects of addiction, tolerance, constipation, drowsiness and impairment of mental activities experienced with common opioid drugs.

BACKGROUND OF THE INVENTION

Neuropathic pain is a chronic condition resulting from damage to sensory nerves in the peripheral nervous system. Common examples of neuropathic pain include injury incurred from stroke and spinal cord injury, phantom limb and causalgia (burning pain) post-nerve damage; primary symptoms include allodynia (sensitivity to stimuli which does not normally evoke pain), hyperalgesia (increased sensitivity to noxious stimuli), paresthesia (tingling sensations), spontaneous nociceptor discharge (ectopic discharge), as well as spontaneous pain. Current clinical treatments for neuropathic pain include synthetic opioids, non-steroidal inflammatory drugs (NSAIDS), and anticonvulsants. However the use of these can be troublesome as tolerance, abuse, and dependence often result from their use. One such tolerance mechanism being studied is the splicing of the mu opioid receptor ($\mu$)—the primary target of common synthetic opioid analgesics morphine, fentanyl, and methadone—which can undergo subunit rearrangement through alternative splicing, producing various receptor variants with differing affinities for these synthetic opioids.

The human body's natural mechanism for analgesia involves the endogenous opioid neuropeptides, composed of three classes: the enkephalins, endorphins, and dynorphins, which are proteolytic fragments of proenkephalin, proopiomelanocortin (POMC), and prodynorphin, respectively. The opioid neuropeptides are characterized by their affinity for the 3 opioid receptors ($\mu$, $\delta$, $\kappa$) present in the central and peripheral nervous system, and by the reversal or block of analgesia by the synthetic opioid antagonist naloxone. The opioid receptors are members of the G-protein coupled receptor (GPCR) class of membrane proteins—composed of 7 transmembrane spanning segments coupled to an inhibitory G protein ($G\alpha_i$), and implicated in various behavioral effects including analgesia, reward, depression, anxiety, and addiction. The endogenous opioid neuropeptides work by binding their cognate GPCR partner, which is coupled to an inhibitory G protein ($G\alpha_i$), eventually leading to the inhibition of N-type $Ca^{2+}$ channels and excitatory neurotransmitter release. Peripheral pain signals are transmitted through afferent nerve fibers into the dorsal root ganglion by way of the spinal cord, and up towards the brain. The action potentials stimulated across these afferent nerve fibers propagate along the central nervous system, triggering the opening of N-type $Ca^{2+}$ channels and the release of excitatory neurotransmitters (Glu, CGRP, substance P)—which activate postsynaptic receptors on upstream neurons, all cooperating to transmit the pain signal. The inhibition of these signals, stimulated by the binding and actions of the endogenous opioids, is one of the body's homeostatic mechanisms to counteract pain.

Opioids are a large class of drugs, used clinically as painkillers that include both plant-derived and synthetic alkaloids and peptides found endogenously in the mammalian brain. While the plant-derived alkaloids have been known and used for thousands of years, the endogenous opioid peptides were discovered only in the mid-1970s. These are known to comprise three distinct gene families: $\beta$-endorphin and other peptides derived from proopiomelanocortin; enkephalins, derived from proenkephalin A; and the dynorphins, derived from proenkephalin B.

Opioid compounds interact with neuronal cells and modulate physiological functions such as nociception. Thus, one of the physiological effects attributed to the opioid system is analgesia.

Endogenous opioids exist in multiple forms in the central nervous system, and include the dynorphins, which are a series of peptides derived from the precursor prodynorphin (proenkephalin B). The first of the dynorphins to be isolated was the 17 amino acid peptide having the structure shown (and designated SEQ ID NO:1), sometimes also referred to as "dynorphin A-(1-17)":

```
                                        (SEQ ID NO: 1)
Tyr-Gly-Gly-Phe-Leu-Arg-Arg-Ile-Arg-Pro-Lys-Leu-

Lys-Trp-Asp-Asn-Gln
```

Within the last decade, various U.S. patents have described and suggested uses of dynorphin.

U.S. Pat. No. 4,396,606, issued Aug. 2, 1983, describes isolation of a compound (sometimes hereinafter called "dynorphin A-(1-13)") with the structure:

```
                                        (SEQ ID NO: 2)
Tyr-Gly-Gly-Phe-Leu-Arg-Arg-Ile-Arg-Pro-Lys-Leu-Lys
```

This fragment of the seventeen amino acid endogenous peptide was found to be substantially more active than the enkephalins and $\beta$-endorphin in a guinea pig ileum test. Compositions containing dynorphin were suggested to be analgesic by virtue of their interaction with opioid receptor sites, and administration in the same manner as other opioid agonists (e.g. morphine) was disclosed.

U.S. Pat. No. 4,462,941, issued Jul. 31, 1984, describes dynorphin amide analogs with ten amino acid residues. These dynorphin A-(1-10) amide analogs do not have significant analgesic activity in opioid tail flick tests (unless given in huge doses where they tend to produce convulsions).

Enkephalin analogues that are conformationally constrained by a cyclic structure (such as with a disulfide bridge) are described by U.S. Pat. No. 4,518,711, issued May 21, 1985. Subsequently, dynorphin analogues have become known that have cysteine replacements at the amino acid residue 5 (usually leucine) and at the amino acid residue 11 (usually lysine). The amino acid residue 8 (usually an isoleucine) and the amino acid residue 13 (usually a lysine) have similarly been replaced by cysteines in a bridged relationship. The bridges, or cyclic structures, appear to assist in stabilizing the dynorphin analogues against in vivo degradations.

Lee et al., International Publication No. WO93/25217, discloses therapeutic uses of certain truncated N-terminal dynorphin A analogues in conjunction with narcotic analgesics in order to potentiate activity of the narcotic analgesic and/or to block withdrawal symptoms. However, uses in conjunction with narcotic analgesics for opioid effects require a presence of opioid drugs.

Opioid drugs are used clinically as painkillers, but their usefulness is limited by the tolerance and dependence that normally develops upon chronic treatment. Tolerance may be defined as an increase in the amount of drug needed to achieve a certain level of analgesia, while dependence manifests itself in the need to continue taking drug to prevent withdrawal symptoms. Despite a great deal of research on these phenomena, little is known about their molecular basis. Opioid drugs, such as, for example, morphine, are addictive and have central opioid side effects such as drowsiness and impairment of mental activity.

Some non-opiate compositions have been suggested for relieving chronic pain, such as experienced as burning or hyperesthesia pain. Thus, U.S. Pat. No. 5,006,510, issued Apr. 9, 1991, describes somatostatin analogue compositions for topical administration in the treatment of pain where opiates do not significantly change the experience of the patient's pain.

Nevertheless, a variety of painful conditions exist that are relatively resistant to analgesic relief by narcotic analgesics such as morphine.

The foregoing discussion of the prior art derives primarily from PCT Published Application WO/96/06626 which describes the use of certain peptides, more specifically, certain analogs of dynorphin A that are truncated, with respect to endogenous dynorphin at the N-terminus for inducing analgesia in a patient experiencing chronic pain. According to the inventors, administration of these particular peptides provides non-opiod analgesia whereby the central nervous system side effects of a drug such as morphine, e.g. drowsiness, impaired mental functioning and the like, are avoided.

SUMMARY OF THE INVENTION

The present invention is based on the discovery of certain dynorphin A analogues act as bradykinin receptor antagonists for relieving pain, without the usual adverse side effects such as addiction, tolerance, drowsiness and impairment of mental activities experienced with common opioid drugs.

BRIEF DESCRIPTION OF THE DRAWINGS

Further features and advantages of the present invention can be seen from the following detailed description, taken in conjunction with the accompanying drawings, wherein:

FIG. 1 plots NOA summary and temperature co-efficient values for LSY1026 and LSY1044;

FIG. 2 plots chemical shift deviation of observed $C^\alpha$ proton values from residual coil values;

FIG. 4 shows cyclic analogs and binding affinity at bradykinin receptors;

FIG. 5 shows cyclic dynorphin A analog;

FIGS. 6A and 6B plot dose-dependent reversal of thermal hyperalegesia and tactile hypersensitivity of varying does of LYS1044;

FIG. 7 plots hindlimb tests by i.th. administration of dynorphin A-(2-13) and/or LYS 1044 in naïve rats;

FIGS. 8A and 8B plot bradykinin-induced plasma extravasion for changes in paw volume;

FIG. 9 shows two acid-labile resins for SPS;

FIG. 10 shows a structure of a protective group in a Fmoc-Gly-OH structure;

FIG. 11 shows an HOAt and neighboring group effect; and

FIG. 12 illustrates a general scheme for solid phase peptides synthesis in accordance with the present invention.

DETAILED DESCRIPTION OF THE INVENTION

Figure 3A:
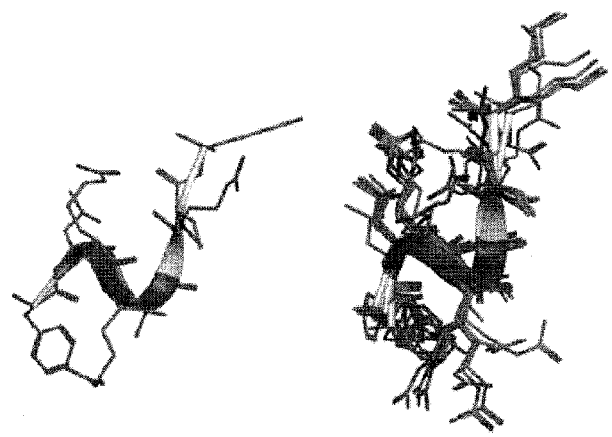
FIGS. 3A and 3B plot lowest energy structure and overall of ten low energy structure of LYS1026(A) and LYS1044 (B)

For the purposes of this disclosure, a "salt" is any acid addition salt, preferably a pharmaceutically acceptable acid addition salt, including but not limited to, halogenic acid salts such as hydrobromic, hydrochloric, hydrofluoric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic orp-toluenesulfonic), acetic, malic, fumaric, succinic, citric, benzoic, gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogenic, di-sulfuric, di-phosphoric or di-organic acid salt. In all cases, the acid addition salt is used as an achiral reagent which is not selected on the basis of any expected or known preference for interaction with or precipitation of a specific optical isomer of the products of this disclosure.

"Pharmaceutically acceptable salt" is meant to indicate those salts which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol 6. 1-19, which is hereby incorporated by reference in its entirety, describes pharmaceutically acceptable salts in detail.

As used herein, the term "daily dose amount" refers to the amount of pramipexole per day that is administered or prescribed to a patient. This amount can be administered in multiple unit doses or in a single unit dose, in a single time during the day or at multiple times during the day.

A "dose amount" as used herein, is generally equal to the dosage of the active ingredient, which may be administered per day. For example, an effective dose amount may be 0.1 to 30 mg/kilo administered 1 to 4 times a day.

The term "unit dose" as used herein may be taken to indicate a discrete amount of the therapeutic composition that contains a predetermined amount of the active compound. The amount of the active compound is generally equal to the dosage of the active ingredient, which may be administered one or more times per day. For example, the unit dose may be a fraction of the desired daily dose which may be given in fractional increments, such as, for example, one-half or one-third the dosage.

"Administering" when used in conjunction with a therapeutic means to administer a therapeutic directly into or onto a target tissue or to administer a therapeutic to a patient whereby the therapeutic positively impacts the tissue to which it is targeted. "Administering" a composition may be accomplished by oral or rectal administration, injection, infusion, inhalation, absorption or by any method in combination with other known techniques. Such combination techniques include heating, radiation and ultrasound.

ABBREVIATIONS used herein include: Ac, acetyl; BK, bradykinin; BR, bradykinin receptor; BSA, bovine serum albumin; CSI, chemical shift index; CVFF, consistent valency force field; DALKD, [des-Arg$^{10}$, Leu$^9$]-kallidin; DIPEA, diisopropylethylamine; DMF, N,N-dimethylformamide; Dyn A, dydnorphin A; Fmoc, 9-fluorenylcarboxymide; HBTU, 2-(1H-benzotriazole-1-yl)-1,1,3,3-tetramethylaminium hexafluorophosphate; HEK, human embryonic kidney; HOBt, N-hydroxybenzotriazole; i.pl., intraplantar; KD, kallidin; NOE, nuclear overhauser effect; NOESY, nuclear overhauser enhancement spectroscopy; RP-HPLC, reverse phase high performance liquid chromatography; SDS, sodium dodecyl sulfate; TFA, trifluoroacetic acid; TIS, triisopropylsilane; TSP, 3-(trimethylsilyl)propionic acid.

We have developed novel non-opioid dynorphin analogs, which interact with the BR receptor to relieve pain. The compounds are novel in the deletion of an arginine residue in position 7 which has been recognized as an essential residue for opioid and non-opioid activities. This deletion has been shown to retain biological activity for the receptor. We also have identified the minimum pharmacophore (combination of more than 2 basic amino acids and 2 hydrophobic amino acids) for the BRs. The series of dynorphin A analogs show therapeutic benefit to modulate pain, since it has been shown that up-regulation of dynorphin causes hyperalgesia by interacting with the bradykinin receptor.

In one aspect of the invention, the novel dynorphin A analogues comprise a [des-Arg$^7$]-dynorphin A analog having the formula $$R^1\text{-}(AA^1\text{-}AA^2)_l\text{-}Pro\text{-}AA^2\text{-}(AA^1\text{-}AA^2)_m \qquad \text{(SEQ ID NO:47)}$$

wherein R$^1$ is Phe, Phe(X), Trp, D-Phe, D-Phe(X), D-Trp, Gly-Phe, Gly-Phe(X), or Gly-Trp and same as AA$^2$ if l=0 and N-terminus is acetylated or a free amine, AA$^1$ is Ile, Leu, Nle, Val, Ala, D-Ile, D-Leu, D-Nle, D-Val, D-Ala, or any hydrophobic amino acids, AA$^2$ is Arg, Lys, His, Orn, or any other basic amino acids, and the AA$^2$ terminus is an acid, 1 and m are 0, 1, or 2.

In the second aspect of the invention, the novel dynorphin A analogues comprise a cyclic dynorphin A analog having the formula $$_c[R^1\text{-}(AA^2\text{-}AA^1)_n\text{-}AA^2\text{-}AA^3]\text{-}AA^2 \qquad \text{(SEQ ID NO:48)}$$

wherein R$^1$ is Phe, Phe(X), Trp, D-Phe, D-Phe(X), D-Trp, Gly-Phe, Gly-Phe(X), or Gly-Trp AA$^1$ is Ile, Leu, Nle, Val, Ala, D-Ile, D-Leu, D-Nle, D-Val, D-Ala, or any other hydrophobic amino acid, AA$^2$ is Arg, Lys, His, Orn, or any other basic amino acids and the AA$^2$ terminus is an acid, AA$^3$ is Asp, Glu or any other amino acid having a side chain acid group, n is 1, or 2. The α-amino group of R$^1$ is involved in a cyclization with the side chain acid of AA$^3$.

In the third aspect of the invention, the novel dynorphin A analogues comprise a cyclic dynorphin A analog having the formula $$(AA^2\text{-}AA^1)_o\text{-}_c[AA^3AA\text{-}AA^1_p\text{-}(AA^2\text{-}AA^1\text{-}AA^2)_q\text{-} \\ AA^1_p\text{-}AA^3]\text{-}AA_2 \qquad \text{(SEQ ID NO:49)}$$

wherein AA$^1$ is Ile, Leu, Nle, Val, Ala, D-Ile, D-Leu, D-Nle, D-Val, D-Ala, or any other hydrophobic amino acid, AA$^2$ is Arg, Lys, His, Orn, or any other basic amino acids and the AA$^2$ terminus is an acid, AA$^3$ is Asp, Glu, Lys, or any other amino acid having a side chain acid group or amino group, o is 0, or 1, p is 0, or 1, q is 1, or 2. The side chain amino or acid group of AA$^3$ is involved in a cyclization with the side chain of counter part amino acid (Lys/Asp, Asp/Lys, etc).

The novel dynorphin A analogues of the present invention were identified through a systematic structure-activity relationship (SAR) study. The study discovered the essential minimum pharmacophore of dynorphin A for bradykinin receptors in the central nervous systems, as well as distinct SAR insights (Tables 1-5). The SAR study showed that the binding affinities at the rat brain bradykinin receptors depend on net charge, location of positive charges, amphipathicity, and pH. Lowering the pH of a binding buffer solution from 7.4 to 6.8 resulted in the increase of binding affinities of the analogs. This result indicates that the electrostatic interaction of dynorphin A analogs with the receptor is a key feature for the bradykinin receptor recognition.

Initially, LYS1026 [dynorphin A (4-11)] and LYS1113 [dynorphin A (9-13)] were identified as minimum pharmacophores for the rat brain bradykinin receptors (Table 1). The SAR results revealed that the receptor recognition predominantly depends on the basicity of the C-terminal amino acid (Tables 2 and 3). When the C-terminal amino acid residue was changed to a hydrophobic amino acid residue (Leu, Ile, etc), or the C-terminal acid function of a basic amino acid was modified to an amide, the binding affinities were decreased dramatically. On the contrary, the N-terminal amino acid residue did not affect the binding affinities (Table 4). Acetylation of a free amino group or inversion of the chirality of an amino acid residue at the N-terminus retained their binding affinities at the rat brain bradykinin receptors. The most important result from our SAR study is that the truncation of an Arg in position 7 does not affect the binding affinity (Table 5). [Des-Arg$^7$]-dynorphin A analogs and their unmodified dynorphin A analogs showed the same range of binding affinities. Specifically, LYS1044, differing from LYS1026 by deleting Arg$^7$ retained good binding affinity for the rat brain bradykinin receptors (Table 1). Therefore, LYS1044 is one preferred compound for developing bradykinin receptor antagonists. LYS1044 is a short heptapeptide including 3 basic amino acids, 3 hydrophobic amino acids, and a proline residue which contributes to a peptide turn structure. Due to the basic and also amphipathic properties, the ligand has the ability to penetrate cell membrane and overcome blood-brain barrier (BBB) without difficulty.

Figure 3B:

In general, truncation of one amino acid residue in the middle of structure can cause significant topographical changes which result in different biological profile, but this is not the case here. To compare the topographical structures of two analogs, an NMR study was performed using membrane-like solvent SDS micelles. Both analogs showed similar NOE results, which indicates that the truncation of an Arg residue does not significantly affect the overall topographical structure. (See FIG. 1). LYS1026 showed two consecutive Type III β-turn (a short 3$_{10}$-helix) at the N-terminal part and a distorted type I β-turn at the C-terminal part whereas the deletion of an Arg residue in LYS1044 resulted a single type III β-turn at the N-terminal part and the same distorted type I β-turn at the C-terminal part. This is shown in FIG. 2 which shows chemical shift deviation of observed Cα protein values from random coil values, and FIG. 3 which shows lowest energy structure and overlay of ten low energy structures of LSY1026(A) and LSY1044(B) from simulated anneal molecular dynamics calculations. It should be noted here that the peptide LYS1044 does not contain Arg (4) residue. All hydrogen atoms are not shown for simplicity. The ribbon diagram shows the secondary structure of the peptide. RMSD between structures are 2.013 Å (A) or 1.694 Å (B) and when all the atoms are considered, but it is reduced significantly to 0.502 Å (A) or 0.155 Å (B) when only backbone atoms are considered.

It was shown that the truncation of an Arg residue in position 7 or the insertion of one more Arg residue in position 7 did not affect the binding affinities and all the [des-Arg$^7$]-dynorphin A or [Arg-Arg]$^9$-dynorphin A analogs retain comparable binding affinities (compare binding affinities of LYS1026, LYS1044, and SH114 in Tables 1 and 5). Two neighboring Arg (net charge increase) seem to be unnecessary for the bradykinin receptor recognition. However, the allocation of the positive charges to retain the amphiphaticity inside can be more significant than net positive charges. For the proper allocation of the positive charges in the ligands, hydrophobic amino acid residues were modified and inserted between the charges retaining the amphiphaticity. Even though these fine modifications resulted in small change of the binding profile, there is a potential to improve the stability of the ligands using non-natural amino acids. Ligand SH145, in which a Leu residue is substituted by a D-Leu residue, retained the same high binding affinity as LYS1044 and showed increase ($t_{1/2>1}$ day for SH145; $t_{1/2}<3$ h for LYS1044) in plasma. The big increase of stability is deemed to be caused by the replacement of non-natural amino acid residue, which is more resistant to aminopeptidases. Since the N-terminal amino acid modifications did not affect binding affinities, it is doable to optimize ligands stability without damaging their activities. Another trial to increase the stability was done by cyclization of the lead compound structure using ring metathesis. Two cyclic ligands were synthesized by solid phase peptide synthesis using Fmoc chemistry on the Wang resin and the ligands were tested for their binding at bradykinin receptors. See FIG. 4. The cyclic ligands lost the binding affinities at bradykinin receptors and these are considered as the result of the loss of amphiphaticity. Therefore we designed and synthesized the cyclic analogs that expose the hydrophobic alkyl chain outside of the cyclic ring and thereby retain the amphiphaticity. This is illustrated in FIG. 5.

A lead compound LYS1044 showed dose dependent antihyperalgesic and anti-allodynic effects on SNL rats, which are a neuropathic pain model, but no toxic effect on rotarod experiment (See FIG. 6). Intrathecal injection of dynorphin A-(2-13) produces disturbances of motor function and antinociception, but spinal LYS1044 does not produce motor impairment and prevents dynorphin A-(2-13)-induced paralysis (See FIG. 7). Intraplantar injection of LYS1044 does not prevent bradykinin-induced plasma extravasation or does not show changes in paw volume (See FIG. 8). This indicates that the activity of LYS1044 is localized in the CNS.

The dynorphin A analogs of the present invention were synthesized by standard solid phase peptide synthesis (details below) using $N^\alpha$-Fmoc-chemistry on amino acid pre-loaded Wang resin (100-200 mesh, Novabiochem) in high yields (overall yield >40%). All the side functional groups of amino acid residues were protected orthogonally to Fmoc-group (ex. Pbf and Boc for Arg and Lys, respectively). Coupling was performed using 3 eq. HBTU/3 eq. HOBt/6eq. DIPEA in DMF for 1 h at rt and $N^\alpha$-Fmoc-group was deprotected by 20% piperidine in DMF for 20 min at rt. In most cases, crude peptides were obtained by cleavage using a 95% TFA solution containing 2.5% TIS and 2.5% water for 3 h in high purity (70-90%) and could be isolated with more than 97% purity by prep. RP-HPLC using gradient (10-40% acetonitrile in water containing 0.1% TFA in 15 min) in a short time (<15 min) owing to their hydrophilic characters. The purified dynorphin A analogs were validated by analytical RP-HPLC and high resolution mass spectroscopy in positive ion mode.

Hypothesis:

While not wishing to be bound by theory, it is believed that the analogues of dynorphin A of the present invention exhibit antagonist activities at the bradykinin receptor that may counteract the pronociceptive effects of elevated dynorphin A levels that occur during chronic pain. The proposed hypothesis is that at low concentrations, dynorphin A's cognate binding partners are the opioid receptors, but when dynorphin A expression is 1 upregulated during conditions of neuropathic pain, these peptides exhibit cross-reactivity with its second molecular target, the bradykinin receptor.

The potential for selective antagonism by a dynorphin A analogue, acting at the bradykinin receptor, to block the pronociceptive and excitatory effects seen in chronic pain models and as an agonist at the opioid receptors, all without interfering with the functions of endogenous bradykinin in the periphery, is a novel approach to chronic pain treatment. The ideal peptide would act as an antagonist at the bradykinin receptors, allowing for control of hyperalgesia and modulation of the pronociceptive actions of dynorphin A during chronic pain.

To that objective, dynorphin A analogues were designed and synthesized via solid phase peptide synthesis, and a structure-activity relationship study was performed with various modifications (truncations, cyclization, retro- & inverso-, unnatural amino acids additions, etc.), to improve binding affinities of dynorphin A at the bradykinin receptor.

EXAMPLES

Experimental Methods

Solid-Phase Peptide Synthesis of Dynorphin a Analogues

The methodology of solid phase peptide synthesis (SPPS) is a repeating cycle of deprotection, coupling, and final cleavage. The initial step involves the attachment of the C-terminal amino acid residue of choice to the resin. Two popular acid-labile resins for SPPS, are the Wang and Rink Amide resins. The Wang resin contains the linker linked to a polystyrene core (4-hydroxybenzyl alcohol moiety) (FIG. 9, left), which is utilized to create a carboxylic acid ($CO_2H$) at the C-terminus upon cleavage of the peptide from the resin. The linker is cleaved from the polystyrene core with treatment of moderate acid, which cleaves the phenyl ether bond between the linker and resin. The Rink Amide resin (FIG. 9, right) is used when one desires to create an amide ($CONH_2$) instead of an acid at the C-terminus of the peptide. The Rink linker is bonded to the Polystyrene core through an ether linkage, which can be cleaved with treatment of mild to moderate acid. Solvents used for Fmoc- and Boc-chemistry, coupling and deprotection reactions, and washing steps were primarily N, N-dimethylformamide (DMF) and dichloromethane (DCM).

In order to prevent polymerization of undesired products, the reactive side groups of amino acids and amino group of incoming amino acid residues must be protected. Protecting groups in the design scheme were designed to be orthogonal to the Fmoc group (See FIG. 10, blocked area), which is removed with base to abstract the acidic proton of the fluorenyl ring system, leading to beta-elimination and formation of $CO_2$ gas and dibenzofluvine; Piperidine (secondary amine) is primarily used for the deprotection of Fmoc groups, as it acts to not only remove the protecting group, but scavenges the dibenzofluvine ring system side-product to prevent undesirable side reactions. As a result of this base-sensitivity, side-chain protecting groups are generally acid-labile (Pbf, t-Bu, and Boc for Arg, Asp, Glu, and Lys, respectively) and removed during the harsh acidic conditions of the cleavage reaction of the peptide from the resin. For cyclic peptides, side amino/acid groups are exposed from orthogonally protected groups before the cleavage and are coupled for cyclization. The deprotection of the Fmoc group relieves the amino group of the N-terminal residue, allowing the $NH_2$ to attack the incoming residue's $CO_2H$, to produce a new peptide linkage through dehydration.

Coupling reagents for SPPS are primarily used for activation of the incoming amino acid, to form a amide bond with the previous residue that is now bound to the resin, and to prevent racemization of the alpha-carbon upon collapse of the tetrahedral intermediate. HBTU, HATU, and HCTU are used to activate the amino acid for attack by the free amine group of the previously attached amino acids are used in ascending order of desired coupling time—each having a higher rate, less epimerization of the alpha-carbon, and greater stability. However, all three of these reagents can react with unprotected amines at the N-terminal end of the chain and prevent further peptide polymerization by forming a guanidine moiety, and must be used in equimolar amount relative to the acid component of the coupling reaction.

To prevent racemization of the alpha carbon after amino acid activation, HOAt is used in conjunction with a primary coupling agent, which acts to prevent epimerzation through the neighboring group effect (FIG. 11), i.e., the interaction of the primary amine with the lone pair on the Nitrogen in the HOAt ring increases the rate of peptide bond formation and prevents epimerization of the alpha-carbon.

To qualitatively monitor the progress of synthesis, the Kaiser and Chloranil tests are utilized after each subsequent coupling and deprotection, which test for a free primary and secondary amine group respectively. The Kaiser test is based on the reaction of ninhydrin with amine functional groups, with primary amines producing a dark violet/blue color; the Chloranil test employs a similar reaction, but is used to test for the presence of a secondary amine such as Proline, which produces a blue color for a positive (free amine) reaction. The general scheme of solid phase peptide synthesis (SPPS) can be seen in FIG. 12.

Purification of dynorphin A analogues.

Crude peptides were dissolved in HPLC-grade $H_2O$ and purified by reversed-phase high performance liquid chromatography (RP-HPLC) (solution A: 0.01% TFA in $H_2O$ and solution B: ACN) on C-18 semi-prep column. Retention times for compounds collected during standard run of 10-90-10% B in 0-40-45 minutes. After purification of desired fraction, acetonitrile (ACN) evaporated under vacuum and solution frozen in −80° C. freezer. Frozen peptide product lyophilized to produce 10-100 mg of product in 30-60% yield as white powder. Peptide product analyzed with RP-HPLC (on analytical C-18 column) and mass spectrometry to confirm purity and structure.

NMR spectroscopy methods.

NMR studies of ligands LYS1026 and LYS1044 in SDS micelles were performed on a Bruker DRX600 (600 MHz) at 25° C. and at pH 5.5. Peptide concentrations for the NMR experiments were 5.8 mM and 6.1 mM for LYS1026 and LYS1044, respectively. The micelle samples were prepared by dissolving the peptides and 50 eq. perdeuterated SDS in 0.6 mL of acetate buffer (10 mM) containing 10% $D_2O$. The pH of the each sample was adjusted to 5.5 by using DCl or NaOD as necessary. Deuterated TSP was added as internal standard for referencing. Two-dimensional NOESY and TOCSY (supporting information) were acquired using standard pulse sequences and processed using XWINNMR (Bruker Inc.) and FELIX2000 (Accelrys Inc., San Diego, Calif.). Mixing times for TOCSY and NOESY spectrum were 60 ms and 300 ms, respectively. All experiments were 750 increments in t1, 16 or 32 scans each, 1.5 s relaxation delay, size 2 or 4K and the spectral processing was with shifted sine bell window multiplications in both dimensions. The water suppression was achieved by using WATER-GATE pulse sequence. Coupling constants (3JαH-NH) were measured from DQF-COSY.

Structure calculation methods.

Distance constraints for the structure calculation were obtained from integral volumes of the NOESY peaks. The NOE integral volumes were classified into strong, medium and weak with 3.0, 4.0 and 5.0 Å as upper bound distance. Molecular dynamics simulation was done with the INSIGHT/DISCOVER package (Accelrys Inc, San Diego, Calif.) with CVFF. All the calculations were done in vacuo. A distance dependent dielectric constant (2.5r where r is the distance in Å) was used. All peptide bonds were constrained to trans conformation by a 100 kcal/mol energetic penalty. Distance restraints with a force constant of 25 kcal/mol were applied in the form of a flat-bottom potential well with a common lower bound of 1.8 Å and an upper bound of 3.0, 4.0 and 5.0 Å, respectively, in accordance with observed weak, moderate or strong NOE intensities. Only the distance restraints from inter-residue NOEs were included in the calculation. Dihedral angle restraints based on $C_αH$ CSI were imposed on the residues displaying negative deviation. Thus for a CSI of >−0.10 ppm, the φ and ψ restraints were in the range −90° to −30° and −60° to 0°, respectively while for a CSI of ≤−0.10 ppm, the corresponding ranges were −150° to −30° for φ and −90° to 1500 for ψ.

Radioligand Competition Binding Assays.

Binding affinities of dynorphin A analogs at the bradykinin receptors were determined by radioligand competition analysis using [$^3$H]DALKD or [$^3$H]BK in rat brain membranes or transfected HEK 293 cells expressing the human B2R. Crude rat brain membranes were pelleted and resuspended in 50 mM Tris buffer containing 50 μg/mL bacitracin, 10 μM captopril, 100 μM PMSF, and 5 mg/mL BSA. 10 concentrations of a test compound were each incubated with 50 μg of membranes and [$^3$H]DALKD (1 nM, 76.0 Ci/mmol) or [$^3$H]BK (1 nM, 85.4 Ci/mmol) at 25° C. for 2 h. Non-specific binding was defined by that in the presence of 10 M KD in all assays. Reactions were terminated by rapid filtration through Whatman GF/B filters presoaked in 1% polyethyleneimine, followed with four washes of 2 mL cold saline. Radioactivity was determined by liquid scintillation counting in a Beckman LS5000 TD. Data were analyzed by non-linear least squares analysis using Graph-Pad Prism (Version 4). Logarithmic values determined from the nonlinear regression analysis of data collected from at least three independent experiments.

Motor Function and Paralysis.

Intrathecal (i.th.) catheterization. While under ketamine/xylazine (80/12 mg/kg, i.p.) anesthesia, some groups of rats were implanted with i.th. catheters (polyethylene 10, 7.8 cm) through atlanto-occipital membrane extended to the level of the lumbar spinal cord for drug administration. Animals were allowed to recover for 7 days. Drugs were injected in a volume of 5 μl, followed by a 1 μl air bubble and a 9 μl saline flush.

Tail-flick test. The hot-water tail-flick test was performed by placing the distal third of the tail in a water bath maintained at 52° C. The latency until tail withdrawal from the bath was determined and compared among the treatments. A 10 sec cutoff was used to avoid tissue damage. Data were converted to percentage of antinociception by the following formula: (response latency−baseline latency)/(cutoff−baseline latency)*100.

Measurement of Rat Paw Oedema and Plasma Extravasation.

Experiments were conducted on non-fasted male Sprague-Dawley rats (250-300 g) kept in a room controlled for temperature (22±2° C.) and illumination (12 h on and 12 h off). Under ketamine/xylazine (80/12 mg/kg, i.p.) anesthesia animals received an injection of Evans Blue (30 mg/mL/kg, i.v.) via tail vein and baseline paw volume for both hindpaws was measured by use of a plethysmometer (Ugo Basile). Animals then received 0.1 mL i.pl. injections in one hindpaw of normal saline (0.9% NaCl) containing BK either alone or mixed with HOE140 or LYS1044 (10 nmol/paw each). The contralateral paw received 0.1 mL saline and was used as a control. Oedema was measured at several 30, 60 and 90 min post i.pl. injections and expressed in mL as the difference (mL) between the test and control paws. Three hours post BK injections, animals were sacrificed and patches (10×5 mm) of the dorsal skin from both hindpaws were collected. The skin patches were then incubated separately in Eppendorf tubes containing 1.8 mL formamide at 60° C. water bath for 24 h to extract the dye. The tissue extraction was then centrifuged at 15000 rpm for 15 min and the supernatant was pipetted to a 96 well plate as triplicates and the absorbance was determined at 620 nm. The difference of the mean absorbance between the two hindpaws of each rat was used to compare the degree of plasma extravasation in different treatment groups.

While the invention has been described as particularly useful for treatment of neuropathic pain, the invention also may be used for treatment of other types of pain including: Nociceptive Pain including "somatic" pain from injury and "visceral" pain (e.g., sustained pain even after an injury heals) and as an example, associated with trauma or with many different types of diseases, such as diabetes, pain syndromes, diabetic neuropathy, trigeminal neuralgia, postherpetic neuralgia ("shingles"), post-stroke pain, and complex regional pain syndromes (also called reflex sympathetic dystrophy or "RSD" and causalgia); and Psychogenic Pain (most patients with chronic pain have some degree of psychological disturbance). The compounds of this invention also may be used in combination with other medications for such types of pain.

Various changes may be made without departing from the spirit and scope of the disclosure.

TABLE 1

Competitve binding analyses of some dynorphin A analogs against [$^3$H]DALKD at brain bradykinin receptors

| Analogs | Gly$^2$ | Gly$^3$ | Phe$^4$ | Leu$^5$ | Arg$^6$ | Arg$^7$ | Ile$^8$ | Arg$^9$ | Pro$^{10}$ | Lys$^{11}$ | Leu$^{12}$ | Lys$^{13}$ | IC$_{50}$ (nM) at pH 7.4, n ≥ 2 | IC$_{50}$ (nM) at pH 6.8, n ≥ 2 |
|---|---|---|---|---|---|---|---|---|---|---|---|---|---|---|
| Dyn (2-13) (SEQ ID NO: 3) | Gly | Gly | Phe | Leu | Arg | Arg | Ile | Arg | Pro | Lys | Leu | Lys | 170 | 21 |
| CYF103 (SEQ ID NO: 4) | Gly | Gly | Phe | Leu | Arg | | Ile | Arg | Pro | Lys | Leu | Lys | | 41 |
| LYS1042 (SEQ ID NO: 5) | | Gly | Phe | Leu | Arg | | Ile | Arg | Pro | Lys | Leu | Lys | 41 | 26 |
| LYS1040 (SEQ ID NO: 6) | | | | Leu | Arg | | Ile | Arg | Pro | Lys | Leu | Lys | 68 | 30 |
| LYS1114 (SEQ ID NO: 7) | | | | | | Arg | Ile | Arg | Pro | Lys | Leu | Lys | | 72 |
| LYS1039 (SEQ ID NO: 8) | | | | | | | Ile | Arg | Pro | Lys | Leu | Lys | 81 | 63 |
| LYS1113 (SEQ ID NO: 9) | | | | | | | | Arg | Pro | Lys | Leu | Lys | | 58 |
| LYS1038 (SEQ ID NO: 10) | | | | | | | | | Pro | Lys | Leu | Lys | 120 | 210 |
| LYS1026 (SEQ ID NO: 11) | | | Phe | Leu | Arg | Arg | Ile | Arg | Pro | Lys | | | 140 | 69 |
| LYS1044 (SEQ ID NO: 12) | | | Phe | Leu | Arg | | Ile | Arg | Pro | Lys | | | 190 | 69 |

TABLE 2

Structure-Activity Relationship (I) at the C-terminus of dynorphin A analogs against [$^3$H]DALKD at rat brain bradykinin receptors

| Analogs | Gly$^2$ | Gly$^3$ | Phe$^4$ | Leu$^5$ | Arg$^6$ | Arg$^7$ | Ile$^8$ | Arg$^9$ | Pro$^{10}$ | Lys$^{11}$ | Leu$^{12}$ | Lys$^{13}$ | IC$_{50}$ (nM) at pH 7.4, n > 2 |
|---|---|---|---|---|---|---|---|---|---|---|---|---|---|
| LYS1035 (SEQ ID NO: 13) | | Gly | Phe | Leu | Arg | | | | | | | | 950 |
| BP006D (SEQ ID NO: 14) | | Gly | Phe | Leu | Arg | Arg | | | | | | | 8100 |
| LYS1004 (SEQ ID NO: 15) | | Gly | Phe | Leu | Arg | Arg | Ile | | | | | | 2300 |
| J104 (SEQ ID NO: 16) | | Gly | Phe | Leu | Arg | Arg | Ile | Arg | | | | | 780 |
| BP1004D (SEQ ID NO: 17) | | Gly | Phe | Leu | Arg | Arg | Ile | Arg | Pro | | | | 1200 |
| LYS1027 (SEQ ID NO: 18) | | Gly | Phe | Leu | Arg | Arg | Ile | Arg | Pro | Lys | | | 130 |

TABLE 2-continued

Structure-Activity Relationship (I) at the C-terminus of dynorphin A analogs against [$^3$H]DALKD at rat brain bradykinin receptors

| Analogs | Gly$^2$ | Gly$^3$ | Phe$^4$ | Leu$^5$ | Arg$^6$ | Arg$^7$ | Ile$^8$ | Arg$^9$ | Pro$^{10}$ | Lys$^{11}$ | Leu$^{12}$ | Lys$^{13}$ | IC$_{50}$ (nM) at pH 7.4, n > 2 |
|---|---|---|---|---|---|---|---|---|---|---|---|---|---|
| LYS1024 (SEQ ID NO: 19) | | Gly | Phe | Leu | Arg | Arg | Ile | Arg | Pro | Lys | Leu | | 280 |
| LYS1021 (SEQ ID NO: 20) | | Gly | Phe | Leu | Arg | Arg | Ile | Arg | Pro | Lys | Leu | Lys | 320 |

TABLE 3

Structure-Activity Relationship (II) at the C-terminus of dynorphin A analogs against [$^3$H]DALKD at rat brain bradykinin receptors

| Analogs | Gly$^2$ | Gly$^3$ | Phe$^4$ | Leu$^5$ | Arg$^6$ | Arg$^7$ | Ile$^8$ | Arg$^9$ | Pro$^{10}$ | Lys$^{11}$ | Leu$^{12}$ | Lys$^{13}$ | IC$_{50}$ (nM) at pH 7.4, N > 2 |
|---|---|---|---|---|---|---|---|---|---|---|---|---|---|
| RK107 (SEQ ID NO: 21) | | | | | | | Ile | Arg | Pro | Lys | Leu-NH$_2$ | | 8700 |
| RK108 (SEQ ID NO: 22) | | | | | | Arg | Ile | Arg | Pro | Lys | Leu-NH$_2$ | | 6300 |
| LYS1022 (SEQ ID NO: 23) | | | | Leu | Arg | Arg | Ile | Arg | Pro | Lys | Leu | | 7100 |
| LYS1026 (SEQ ID NO: 11) | | | Phe | Leu | Arg | Arg | Ile | Arg | Pro | Lys | | | 140 |
| S1F (SEQ ID NO: 24) | | | Phe | Leu | Arg | Arg | Ile | Arg | Pro | Lys-NH$_2$ | | | 6800 |
| AP107-1 (SEQ ID NO: 25) | | | Ac-Phe | Leu | Arg | | Ile | Arg | Pro | Lys | | | 120 |
| AP111 (SEQ ID NO: 26) | | | Ac-Phe | Leu | Arg | | Ile | Arg | Pro | DLys | | | 550 |
| LYS1035 (SEQ ID NO: 13) | | Gly | Phe | Leu | Arg | | | | | | | | 950 |
| LYS1031 (SEQ ID NO: 27) | | Gly | Phe | Leu | Arg-NH$_2$ | | | | | | | | >10,000 |

TABLE 4

Structure-Activity Relationship at the N-terminus of dynorphin A analogs against [$^3$H]DALKD at rat brain bradykinin receptors

| Analogs | Gly$^2$ | Gly$^3$ | Phe$^4$ | Leu$^5$ | Arg$^6$ | Arg$^7$ | Ile$^8$ | Arg$^9$ | Pro$^{10}$ | Lys$^{11}$ | Leu$^{12}$ | Lys$^{13}$ | IC$_{50}$ (nM) at pH 7.4, N > 2 |
|---|---|---|---|---|---|---|---|---|---|---|---|---|---|
| AN109 (SEQ ID NO: 28) | | | Ac- | Nle | | Nle | | Arg | | | | | 210 |
| AP107-1 (SEQ ID NO: 25) | | | Ac- | | | | | | | | | | 120 |
| AP107-4 (SEQ ID NO: 29) | | | Ac-DPhe | | | | | | | | | | 360 |
| AN104 (SEQ ID NO: 30) | | | | | | | | Arg | | | | | 210 |
| AP106-1 (SEQ ID NO: 31) | | | Ac- | | | | | Arg | | | | | 140 |
| AP106-4 (SEQ ID NO: 32) | | | Ac-DPhe | | | | | Arg | | | | | 140 |
| AN108-1 (SEQ ID NO: 33) | | | Ac- | Nle | | Nle | | Arg | | | | | 140 |
| AN108-4 (SEQ ID NO: 34) | | | Ac-DPhe | Nle | | Nle | | Arg | | | | | 54 |

TABLE 5

Binding affinities of [Des-Arg⁷]-dynorphin A anlaogs and [Arg-Arg]⁷-dynorphin A analog against [³H]DALKD at rat brain bradykinin receptors

| Analogs | Gly² | Gly³ | Phe⁴ | Leu⁵ | Arg⁶ | Arg⁷ | Ile⁸ | Arg⁹ | Pro¹⁰ | Lys¹¹ | Leu¹² | Lys¹³ | $IC_{50}$ (nM) at pH 7.4, N > 2 |
|---|---|---|---|---|---|---|---|---|---|---|---|---|---|
| J101 (SEQ ID NO: 35) | | Gly | Phe | Leu | Arg | | Ile | Arg | | | | | 620 |
| LYS1043 (SEQ ID NO: 36) | | | | Leu | Arg | | Ile | Arg | Pro | Lys | | | 180 |
| LYS1045 (SEQ ID NO: 37) | | Gly | Phe | Leu | Arg | | Ile | Arg | Pro | Lys | | | 130 |
| LYS1040 (SEQ ID NO: 6) | | | | Leu | Arg | | Ile | Arg | Pro | Lys | Leu | Lys | 68 |
| LYS1042 (SEQ ID NO: 5) | | Gly | Phe | Leu | Arg | | Ile | Arg | Pro | Lys | Leu | Lys | 43 |
| CYF103 (SEQ ID NO: 4) | Gly | Gly | Phe | Leu | Arg | | Ile | Arg | Pro | Lys | Leu | Lys | 41 at pH 6.8 |
| SH114 (SEQ ID NO: 38) | | | Phe | Leu | Arg | Arg | Ile | Arg-Arg | Pro | Lys | | | 74 at pH 6.8 |

TABLE 6

Binding affinities of modified dynorphin A anlaogs against [³H]DALKD at rat brain bradykinin receptors

| Analogs | Gly² | Gly³ | Phe⁴ | Leu⁵ | Arg⁶ | Arg⁷ | Ile⁸ | Arg⁹ | Pro¹⁰ | Lys¹¹ | Leu¹² | Lys¹³ | $IC_{50}$ (nM) at pH 7.4, N > 2 |
|---|---|---|---|---|---|---|---|---|---|---|---|---|---|
| SH124 (SEQ ID NO: 39) | | | | | | | Nle | Lys | | | Nle | | 78 at pH 6.8 |
| LYS1107 (SEQ ID NO: 40) | | | | | | | | | | | Nle | | 72 |
| AN101 (SEQ ID NO: 41) | | | | | | | Nle | | | | | | 140 |
| AN102 (SEQ ID NO: 42) | | | | Nle | | | | | | | | | 102 |
| AN103 (SEQ ID NO: 43) | | | Trp | | | | | | | | | | 190 |
| AN104 (SEQ ID NO: 30) | | | | | | | | | | Arg | | | 210 |
| AN105 (SEQ ID NO: 44) | | | | Ile | | | | | | Arg | | | 110 |
| AN106 (SEQ ID NO: 45) | | | | | | | | Leu | | Arg | | | 100 |
| SH145 (SEQ ID NO: 46) | | | | DLeu | | | | | | | | | 99 at pH 6.8 |

---

The invention claimed is:

1. A peptide consisting of an amino acid sequence selected from the group consisting of SEQ ID NOs: 4-6, 28, 30, 33, 34, and 36-45.

2. The peptide of claim 1, wherein said peptide is selected from the group consisting of SEQ ID NOs: 4, 5, 28, 33, 34, and 37-42.

3. A pharmaceutical composition comprising a peptide of claim 1 or a pharmaceutically acceptable salt thereof.

4. The pharmaceutical composition of claim 3, wherein said pharmaceutical composition further comprises a pharmaceutically acceptable carrier.

5. A method for treating pain in a subject, said method comprising administering to a subject in need of pain treatment a peptide of claim 1.

6. The method of claim 5, wherein said peptide is administered 1 to 4 times per day, with a total dose of 0.1 to 30.0 mg/kg.

7. The method of claim 5, wherein the pain is selected from the group consisting of nociceptive pain, somatic pain, visceral pain, neuropathic pain, pain syndrome, pain associated with diabetic neuropathy, trigeminal neuralgia, postherpetic neuralgia, post-stroke pain, complex regional pain syndrome, reflex sympathetic dystrophy, causalgia, psychogenic pain, or a combination thereof.

8. A peptide consisting of the amino acid sequence of SEQ ID NO: 46.

* * * * *

SEQUENCE LISTING

<160> NUMBER OF SEQ ID NOS: 49

<210> SEQ ID NO 1
<211> LENGTH: 17
<212> TYPE: PRT
<213> ORGANISM: Homo sapiens

<400> SEQUENCE: 1

Tyr Gly Gly Phe Leu Arg Arg Ile Arg Pro Lys Leu Lys Trp Asp Asn
1               5                   10                  15

Gln

<210> SEQ ID NO 2
<211> LENGTH: 13
<212> TYPE: PRT
<213> ORGANISM: Homo sapiens

<400> SEQUENCE: 2

Tyr Gly Gly Phe Leu Arg Arg Ile Arg Pro Lys Leu Lys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Dyn (2-13)

<400> SEQUENCE: 3

Gly Gly Phe Leu Arg Arg Ile Arg Pro Lys Leu Lys
1               5                   10

<210> SEQ ID NO 4
<211> LENGTH: 11
<212> TYPE: PRT
<213> ORGANISM: Artificial Sequence
<220> FEATURE:
<223> OTHER INFORMATION: CYF103

<400> SEQUENCE: 4

Gly Gly Phe Leu Arg Ile Arg Pro Lys Leu Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: LYS1042

<400> SEQUENCE: 5

Gly Phe Leu Arg Ile Arg Pro Lys Leu Lys
1               5                   10

<210> SEQ ID NO 6
<211> LENGTH: 8
<212> TYPE: PRT
<213> ORGANISM: Artificial Sequence
<220> FEATURE:
<223> OTHER INFORMATION: LYS1040

<400> SEQUENCE: 6

Leu Arg Ile Arg Pro Lys Leu Lys
1               5

<210> SEQ ID NO 7
<211> LENGTH: 7
<212> TYPE: PRT
<213> ORGANISM: Artificial Sequence
<220> FEATURE:
<223> OTHER INFORMATION: LYS1114

<400> SEQUENCE: 7

Arg Ile Arg Pro Lys Leu Lys
1               5

<210> SEQ ID NO 8
<211> LENGTH: 6
<212> TYPE: PRT
<213> ORGANISM: Artificial Sequence
<220> FEATURE:
<223> OTHER INFORMATION: LYS1039

<400> SEQUENCE: 8

Ile Arg Pro Lys Leu Lys

```
1               5

<210> SEQ ID NO 9
<211> LENGTH: 5
<212> TYPE: PRT
<213> ORGANISM: Artificial Sequence
<220> FEATURE:
<223> OTHER INFORMATION: LYS1113

<400> SEQUENCE: 9

Arg Pro Lys Leu Lys
1               5

<210> SEQ ID NO 10
<211> LENGTH: 4
<212> TYPE: PRT
<213> ORGANISM: Artificial Sequence
<220> FEATURE:
<223> OTHER INFORMATION: LYS1038

<400> SEQUENCE: 10

Pro Lys Leu Lys
1

<210> SEQ ID NO 11
<211> LENGTH: 8
<212> TYPE: PRT
<213> ORGANISM: Artificial Sequence
<220> FEATURE:
<223> OTHER INFORMATION: LYS1026

<400> SEQUENCE: 11

Phe Leu Arg Arg Ile Arg Pro Lys
1               5

<210> SEQ ID NO 12
<211> LENGTH: 7
<212> TYPE: PRT
<213> ORGANISM: Artificial Sequence
<220> FEATURE:
<223> OTHER INFORMATION: LYS1044

<400> SEQUENCE: 12

Phe Leu Arg Ile Arg Pro Lys
1               5

<210> SEQ ID NO 13
<211> LENGTH: 4
<212> TYPE: PRT
<213> ORGANISM: Artificial Sequence
<220> FEATURE:
<223> OTHER INFORMATION: LYS1035

<400> SEQUENCE: 13

Gly Phe Leu Arg
1

<210> SEQ ID NO 14
<211> LENGTH: 5
<212> TYPE: PRT
<213> ORGANISM: Artificial Sequence
<220> FEATURE:
<223> OTHER INFORMATION: BP006D

<400> SEQUENCE: 14

Gly Phe Leu Arg Arg
1               5
```

<210> SEQ ID NO 15
<211> LENGTH: 6
<212> TYPE: PRT
<213> ORGANISM: Artificial Sequence
<220> FEATURE:
<223> OTHER INFORMATION: LYS1004

<400> SEQUENCE: 15

Gly Phe Leu Arg Arg Ile
1               5

<210> SEQ ID NO 16
<211> LENGTH: 7
<212> TYPE: PRT
<213> ORGANISM: Artificial Sequence
<220> FEATURE:
<223> OTHER INFORMATION: J104

<400> SEQUENCE: 16

Gly Phe Leu Arg Arg Ile Arg
1               5

<210> SEQ ID NO 17
<211> LENGTH: 8
<212> TYPE: PRT
<213> ORGANISM: Artificial Sequence
<220> FEATURE:
<223> OTHER INFORMATION: BP1004D

<400> SEQUENCE: 17

Gly Phe Leu Arg Arg Ile Arg Pro
1               5

<210> SEQ ID NO 18
<211> LENGTH: 9
<212> TYPE: PRT
<213> ORGANISM: Artificial Sequence
<220> FEATURE:
<223> OTHER INFORMATION: LYS1027

<400> SEQUENCE: 18

Gly Phe Leu Arg Arg Ile Arg Pro Lys
1               5

<210> SEQ ID NO 19
<211> LENGTH: 10
<212> TYPE: PRT
<213> ORGANISM: Artificial Sequence
<220> FEATURE:
<223> OTHER INFORMATION: LYS1024

<400> SEQUENCE: 19

Gly Phe Leu Arg Arg Ile Arg Pro Lys Leu
1               5                   10

<210> SEQ ID NO 20
<211> LENGTH: 11
<212> TYPE: PRT
<213> ORGANISM: Artificial Sequence
<220> FEATURE:
<223> OTHER INFORMATION: LYS1021

<400> SEQUENCE: 20

Gly Phe Leu Arg Arg Ile Arg Pro Lys Leu Lys
1               5                   10

<210> SEQ ID NO 21
<211> LENGTH: 5
<212> TYPE: PRT
<213> ORGANISM: Artificial Sequence
<220> FEATURE:
<223> OTHER INFORMATION: RK107
<220> FEATURE:
<221> NAME/KEY: MISC_FEATURE
<222> LOCATION: (5)..(5)
<223> OTHER INFORMATION: Terminated with -NH2

<400> SEQUENCE: 21

Ile Arg Pro Lys Leu
1               5

<210> SEQ ID NO 22
<211> LENGTH: 6
<212> TYPE: PRT
<213> ORGANISM: Artificial Sequence
<220> FEATURE:
<223> OTHER INFORMATION: RK108
<220> FEATURE:
<221> NAME/KEY: MISC_FEATURE
<222> LOCATION: (6)..(6)
<223> OTHER INFORMATION: Terminated with -NH2

<400> SEQUENCE: 22

Arg Ile Arg Pro Lys Leu
1               5

<210> SEQ ID NO 23
<211> LENGTH: 8
<212> TYPE: PRT
<213> ORGANISM: Artificial Sequence
<220> FEATURE:
<223> OTHER INFORMATION: LYS1022

<400> SEQUENCE: 23

Leu Arg Arg Ile Arg Pro Lys Leu
1               5

<210> SEQ ID NO 24
<211> LENGTH: 8
<212> TYPE: PRT
<213> ORGANISM: Artificial Sequence
<220> FEATURE:
<223> OTHER INFORMATION: SIF
<220> FEATURE:
<221> NAME/KEY: MISC_FEATURE
<222> LOCATION: (8)..(8)
<223> OTHER INFORMATION: Terminated with -NH2

<400> SEQUENCE: 24

Phe Leu Arg Arg Ile Arg Pro Lys
1               5

<210> SEQ ID NO 25
<211> LENGTH: 7
<212> TYPE: PRT
<213> ORGANISM: Artificial Sequence
<220> FEATURE:
<223> OTHER INFORMATION: AP107-1
<220> FEATURE:
<221> NAME/KEY: MISC_FEATURE
<222> LOCATION: (1)..(1)
<223> OTHER INFORMATION: Acylated

<400> SEQUENCE: 25

Phe Leu Arg Ile Arg Pro Lys

```
<210> SEQ ID NO 26
<211> LENGTH: 7
<212> TYPE: PRT
<213> ORGANISM: Artificial Sequence
<220> FEATURE:
<223> OTHER INFORMATION: AP111
<220> FEATURE:
<221> NAME/KEY: MISC_FEATURE
<222> LOCATION: (1)..(1)
<223> OTHER INFORMATION: Acylated
<220> FEATURE:
<221> NAME/KEY: MISC_FEATURE
<222> LOCATION: (7)..(7)
<223> OTHER INFORMATION: D-Isomer

<400> SEQUENCE: 26

Phe Leu Arg Ile Arg Pro Lys
1               5

<210> SEQ ID NO 27
<211> LENGTH: 4
<212> TYPE: PRT
<213> ORGANISM: Artificial Sequence
<220> FEATURE:
<223> OTHER INFORMATION: LYS1031
<220> FEATURE:
<221> NAME/KEY: MISC_FEATURE
<222> LOCATION: (4)..(4)
<223> OTHER INFORMATION: Terminated with -NH2

<400> SEQUENCE: 27

Gly Phe Leu Arg
1

<210> SEQ ID NO 28
<211> LENGTH: 8
<212> TYPE: PRT
<213> ORGANISM: Artificial Sequence
<220> FEATURE:
<223> OTHER INFORMATION: AN109
<220> FEATURE:
<221> NAME/KEY: MISC_FEATURE
<222> LOCATION: (1)..(1)
<223> OTHER INFORMATION: Acylated
<220> FEATURE:
<221> NAME/KEY: MISC_FEATURE
<222> LOCATION: (3)..(3)
<223> OTHER INFORMATION: Norleucine in place of isoleucine
<220> FEATURE:
<221> NAME/KEY: MISC_FEATURE
<222> LOCATION: (5)..(5)
<223> OTHER INFORMATION: Norleucine in place of isoleucine

<400> SEQUENCE: 28

Gly Phe Xaa Arg Xaa Arg Pro Arg
1               5

<210> SEQ ID NO 29
<211> LENGTH: 7
<212> TYPE: PRT
<213> ORGANISM: Artificial Sequence
<220> FEATURE:
<223> OTHER INFORMATION: AP107-4
<220> FEATURE:
<221> NAME/KEY: MISC_FEATURE
<222> LOCATION: (1)..(1)
<223> OTHER INFORMATION: Acylated
<220> FEATURE:
<221> NAME/KEY: MISC_FEATURE
<222> LOCATION: (1)..(1)
```

```
<223> OTHER INFORMATION: D-Isomer

<400> SEQUENCE: 29

Phe Leu Arg Ile Arg Pro Lys
1               5

<210> SEQ ID NO 30
<211> LENGTH: 7
<212> TYPE: PRT
<213> ORGANISM: Artificial Sequence
<220> FEATURE:
<223> OTHER INFORMATION: AN104

<400> SEQUENCE: 30

Phe Leu Arg Ile Arg Pro Arg
1               5

<210> SEQ ID NO 31
<211> LENGTH: 7
<212> TYPE: PRT
<213> ORGANISM: Artificial Sequence
<220> FEATURE:
<223> OTHER INFORMATION: AN106-1
<220> FEATURE:
<221> NAME/KEY: MISC_FEATURE
<222> LOCATION: (1)..(1)
<223> OTHER INFORMATION: Acylated

<400> SEQUENCE: 31

Phe Leu Arg Ile Arg Pro Arg
1               5

<210> SEQ ID NO 32
<211> LENGTH: 7
<212> TYPE: PRT
<213> ORGANISM: Artificial Sequence
<220> FEATURE:
<223> OTHER INFORMATION: AN106-4
<220> FEATURE:
<221> NAME/KEY: MISC_FEATURE
<222> LOCATION: (1)..(1)
<223> OTHER INFORMATION: Acylated
<220> FEATURE:
<221> NAME/KEY: MISC_FEATURE
<222> LOCATION: (1)..(1)
<223> OTHER INFORMATION: D-Isomer

<400> SEQUENCE: 32

Phe Leu Arg Ile Arg Pro Arg
1               5

<210> SEQ ID NO 33
<211> LENGTH: 7
<212> TYPE: PRT
<213> ORGANISM: Artificial Sequence
<220> FEATURE:
<223> OTHER INFORMATION: AN108-1
<220> FEATURE:
<221> NAME/KEY: MISC_FEATURE
<222> LOCATION: (1)..(1)
<223> OTHER INFORMATION: Acylated
<220> FEATURE:
<221> NAME/KEY: MISC_FEATURE
<222> LOCATION: (2)..(2)
<223> OTHER INFORMATION: Norleucine
<220> FEATURE:
<221> NAME/KEY: MISC_FEATURE
<222> LOCATION: (4)..(4)
<223> OTHER INFORMATION: Norleucine

<400> SEQUENCE: 33
```

Phe Xaa Arg Xaa Arg Pro Arg
1               5

<210> SEQ ID NO 34
<211> LENGTH: 7
<212> TYPE: PRT
<213> ORGANISM: Artificial Sequence
<220> FEATURE:
<223> OTHER INFORMATION: AN108-4
<220> FEATURE:
<221> NAME/KEY: MISC_FEATURE
<222> LOCATION: (1)..(1)
<223> OTHER INFORMATION: Acylated
<220> FEATURE:
<221> NAME/KEY: MISC_FEATURE
<222> LOCATION: (1)..(1)
<223> OTHER INFORMATION: D-Isomer
<220> FEATURE:
<221> NAME/KEY: MISC_FEATURE
<222> LOCATION: (2)..(2)
<223> OTHER INFORMATION: Norleucine
<220> FEATURE:
<221> NAME/KEY: MISC_FEATURE
<222> LOCATION: (4)..(4)
<223> OTHER INFORMATION: Norleucine

<400> SEQUENCE: 34

Phe Xaa Arg Xaa Arg Pro Arg
1               5

<210> SEQ ID NO 35
<211> LENGTH: 6
<212> TYPE: PRT
<213> ORGANISM: Artificial Sequence
<220> FEATURE:
<223> OTHER INFORMATION: J101

<400> SEQUENCE: 35

Gly Phe Leu Arg Ile Arg
1               5

<210> SEQ ID NO 36
<211> LENGTH: 6
<212> TYPE: PRT
<213> ORGANISM: Artificial Sequence
<220> FEATURE:
<223> OTHER INFORMATION: LYS1043

<400> SEQUENCE: 36

Leu Arg Ile Arg Pro Lys
1               5

<210> SEQ ID NO 37
<211> LENGTH: 8
<212> TYPE: PRT
<213> ORGANISM: Artificial Sequence
<220> FEATURE:
<223> OTHER INFORMATION: LYS1045

<400> SEQUENCE: 37

Gly Phe Leu Arg Ile Arg Pro Lys
1               5

<210> SEQ ID NO 38
<211> LENGTH: 9
<212> TYPE: PRT
<213> ORGANISM: Artificial Sequence
<220> FEATURE:
<223> OTHER INFORMATION: SH114

```
<400> SEQUENCE: 38

Phe Leu Arg Arg Ile Arg Arg Pro Lys
1               5

<210> SEQ ID NO 39
<211> LENGTH: 6
<212> TYPE: PRT
<213> ORGANISM: Artificial Sequence
<220> FEATURE:
<223> OTHER INFORMATION: SH124
<220> FEATURE:
<221> NAME/KEY: MISC_FEATURE
<222> LOCATION: (1)..(1)
<223> OTHER INFORMATION: Norleucine
<220> FEATURE:
<221> NAME/KEY: MISC_FEATURE
<222> LOCATION: (5)..(5)
<223> OTHER INFORMATION: Norleucine

<400> SEQUENCE: 39

Xaa Lys Pro Lys Xaa Lys
1               5

<210> SEQ ID NO 40
<211> LENGTH: 4
<212> TYPE: PRT
<213> ORGANISM: Artificial Sequence
<220> FEATURE:
<223> OTHER INFORMATION: LYS1107
<220> FEATURE:
<221> NAME/KEY: MISC_FEATURE
<222> LOCATION: (3)..(3)
<223> OTHER INFORMATION: Norleucine

<400> SEQUENCE: 40

Pro Lys Xaa Lys
1

<210> SEQ ID NO 41
<211> LENGTH: 7
<212> TYPE: PRT
<213> ORGANISM: Artificial Sequence
<220> FEATURE:
<223> OTHER INFORMATION: AN101
<220> FEATURE:
<221> NAME/KEY: MISC_FEATURE
<222> LOCATION: (4)..(4)
<223> OTHER INFORMATION: Norleucine

<400> SEQUENCE: 41

Phe Leu Arg Xaa Arg Pro Lys
1               5

<210> SEQ ID NO 42
<211> LENGTH: 7
<212> TYPE: PRT
<213> ORGANISM: Artificial Sequence
<220> FEATURE:
<223> OTHER INFORMATION: AN102
<220> FEATURE:
<221> NAME/KEY: MISC_FEATURE
<222> LOCATION: (2)..(2)
<223> OTHER INFORMATION: Norleucine

<400> SEQUENCE: 42

Phe Xaa Arg Ile Arg Pro Lys
1               5
```

```
<210> SEQ ID NO 43
<211> LENGTH: 7
<212> TYPE: PRT
<213> ORGANISM: Artificial Sequence
<220> FEATURE:
<223> OTHER INFORMATION: AN103

<400> SEQUENCE: 43

Trp Leu Arg Ile Arg Pro Lys
1               5

<210> SEQ ID NO 44
<211> LENGTH: 7
<212> TYPE: PRT
<213> ORGANISM: Artificial Sequence
<220> FEATURE:
<223> OTHER INFORMATION: AN105

<400> SEQUENCE: 44

Phe Ile Arg Ile Arg Pro Arg
1               5

<210> SEQ ID NO 45
<211> LENGTH: 7
<212> TYPE: PRT
<213> ORGANISM: Artificial Sequence
<220> FEATURE:
<223> OTHER INFORMATION: AN106

<400> SEQUENCE: 45

Phe Leu Arg Leu Arg Pro Arg
1               5

<210> SEQ ID NO 46
<211> LENGTH: 7
<212> TYPE: PRT
<213> ORGANISM: Artificial Sequence
<220> FEATURE:
<223> OTHER INFORMATION: SH145
<220> FEATURE:
<221> NAME/KEY: MISC_FEATURE
<222> LOCATION: (2)..(2)
<223> OTHER INFORMATION: D-Isomer

<400> SEQUENCE: 46

Phe Leu Arg Ile Arg Pro Lys
1               5

<210> SEQ ID NO 47
<211> LENGTH: 15
<212> TYPE: PRT
<213> ORGANISM: Artificial Sequence
<220> FEATURE:
<223> OTHER INFORMATION: [des-Arg7]-dynorphin A analog
<220> FEATURE:
<221> NAME/KEY: MISC_FEATURE
<222> LOCATION: (1)..(1)
<223> OTHER INFORMATION: Phe, Phe(X), Trp, D-Phe, D-Phe(X), D-Trp,
      Gly-Phe, Gly-Phe(X), or Gly-Trp and same as AA2 if l=0 and
      N-terminus is acetylated or a free amine
<220> FEATURE:
<221> NAME/KEY: MISC_FEATURE
<222> LOCATION: (2)..(2)
<223> OTHER INFORMATION: can be absent or Ile, Leu, Nle, Val, Ala,
      D-Ile, D-Leu, D-Nle, D-Val, D-Ala, or any hydrophobic amino acids
<220> FEATURE:
<221> NAME/KEY: MISC_FEATURE
<222> LOCATION: (3)..(3)
<223> OTHER INFORMATION: can be absent or Arg, Lys, His, Orn, or any
      other basic amino acids
<220> FEATURE:
```

```
<221> NAME/KEY: MISC_FEATURE
<222> LOCATION: (4)..(4)
<223> OTHER INFORMATION: can be absent or Ile, Leu, Nle, Val, Ala,
      D-Ile, D-Leu, D-Nle, D-Val, D-Ala, or any hydrophobic amino acids
<220> FEATURE:
<221> NAME/KEY: MISC_FEATURE
<222> LOCATION: (5)..(5)
<223> OTHER INFORMATION: can be absent or Arg, Lys, His, Orn, or any
      other basic amino acids
<220> FEATURE:
<221> NAME/KEY: MISC_FEATURE
<222> LOCATION: (6)..(6)
<223> OTHER INFORMATION: can be absent or Ile, Leu, Nle, Val, Ala,
      D-Ile, D-Leu, D-Nle, D-Val, D-Ala, or any hydrophobic amino acids
<220> FEATURE:
<221> NAME/KEY: MISC_FEATURE
<222> LOCATION: (7)..(7)
<223> OTHER INFORMATION: can be absent or Arg, Lys, His, Orn, or any
      other basic amino acids
<220> FEATURE:
<221> NAME/KEY: MISC_FEATURE
<222> LOCATION: (9)..(9)
<223> OTHER INFORMATION: can be absent or Arg, Lys, His, Orn, or any
      other basic amino acids
<220> FEATURE:
<221> NAME/KEY: MISC_FEATURE
<222> LOCATION: (10)..(10)
<223> OTHER INFORMATION: can be absent or Ile, Leu, Nle, Val, Ala,
      D-Ile, D-Leu, D-Nle, D-Val, D-Ala, or any hydrophobic amino acids
<220> FEATURE:
<221> NAME/KEY: MISC_FEATURE
<222> LOCATION: (11)..(11)
<223> OTHER INFORMATION: can be absent or Arg, Lys, His, Orn, or any
      other basic amino acids
<220> FEATURE:
<221> NAME/KEY: MISC_FEATURE
<222> LOCATION: (12)..(12)
<223> OTHER INFORMATION: can be absent or Ile, Leu, Nle, Val, Ala,
      D-Ile, D-Leu, D-Nle, D-Val, D-Ala, or any hydrophobic amino acids
<220> FEATURE:
<221> NAME/KEY: MISC_FEATURE
<222> LOCATION: (13)..(13)
<223> OTHER INFORMATION: can be absent or Arg, Lys, His, Orn, or any
      other basic amino acids
<220> FEATURE:
<221> NAME/KEY: MISC_FEATURE
<222> LOCATION: (14)..(14)
<223> OTHER INFORMATION: can be absent or Ile, Leu, Nle, Val, Ala,
      D-Ile, D-Leu, D-Nle, D-Val, D-Ala, or any hydrophobic amino acids
<220> FEATURE:
<221> NAME/KEY: MISC_FEATURE
<222> LOCATION: (15)..(15)
<223> OTHER INFORMATION: can be absent or Arg, Lys, His, Orn, or any
      other basic amino acids

<400> SEQUENCE: 47

Xaa Xaa Xaa Xaa Xaa Xaa Xaa Pro Xaa Xaa Xaa Xaa Xaa Xaa Xaa
1               5                   10                  15

<210> SEQ ID NO 48
<211> LENGTH: 8
<212> TYPE: PRT
<213> ORGANISM: Artificial Sequence
<220> FEATURE:
<223> OTHER INFORMATION: cyclic dynorphin A analog
<220> FEATURE:
<221> NAME/KEY: MISC_FEATURE
<222> LOCATION: (1)..(1)
<223> OTHER INFORMATION: Phe, Phe(X), Trp, D-Phe, D-Phe(X), D-Trp,
      Gly-Phe, Gly-Phe(X), or Gly-Trp
<220> FEATURE:
<221> NAME/KEY: MISC_FEATURE
<222> LOCATION: (1)..(7)
<223> OTHER INFORMATION: Attached to form a cyclic peptide
<220> FEATURE:
<221> NAME/KEY: MISC_FEATURE
<222> LOCATION: (1)..(7)
```

```
<223> OTHER INFORMATION: The alpha-amino group of Xaa1 is involved in a
      cyclization with the side chain acid of Xaa7 to form a cyclic
      peptide
<220> FEATURE:
<221> NAME/KEY: MISC_FEATURE
<222> LOCATION: (2)..(2)
<223> OTHER INFORMATION: Arg, Lys, His, Orn, or any other basic amino
      acids
<220> FEATURE:
<221> NAME/KEY: MISC_FEATURE
<222> LOCATION: (3)..(3)
<223> OTHER INFORMATION: Ile, Leu, Nle, Val, Ala, D-Ile, D-Leu, D-Nle,
      D-Val, D-Ala, or any other hydrophobic amino acid
<220> FEATURE:
<221> NAME/KEY: MISC_FEATURE
<222> LOCATION: (4)..(4)
<223> OTHER INFORMATION: can be absent or Arg, Lys, His, Orn, or any
      other basic amino acids
<220> FEATURE:
<221> NAME/KEY: MISC_FEATURE
<222> LOCATION: (5)..(5)
<223> OTHER INFORMATION: can be absent or Ile, Leu, Nle, Val, Ala,
      D-Ile, D-Leu, D-Nle, D-Val, D-Ala, or any other hydrophobic amino
      acid
<220> FEATURE:
<221> NAME/KEY: MISC_FEATURE
<222> LOCATION: (6)..(6)
<223> OTHER INFORMATION: Arg, Lys, His, Orn, or any other basic amino
      acids
<220> FEATURE:
<221> NAME/KEY: MISC_FEATURE
<222> LOCATION: (7)..(7)
<223> OTHER INFORMATION: Asp, Glu or any other amino acid having a side
      chain acid group
<220> FEATURE:
<221> NAME/KEY: MISC_FEATURE
<222> LOCATION: (8)..(8)
<223> OTHER INFORMATION: Arg, Lys, His, Orn, or any other basic amino
      acids

<400> SEQUENCE: 48

Xaa Xaa Xaa Xaa Xaa Xaa Xaa Xaa
1               5

<210> SEQ ID NO 49
<211> LENGTH: 13
<212> TYPE: PRT
<213> ORGANISM: Artificial Sequence
<220> FEATURE:
<223> OTHER INFORMATION: cyclic dynorphin A analog 2
<220> FEATURE:
<221> NAME/KEY: MISC_FEATURE
<222> LOCATION: (1)..(1)
<223> OTHER INFORMATION: can be absent or Arg, Lys, His, Orn, or any
      other basic amino acids and the terminus is an acid
<220> FEATURE:
<221> NAME/KEY: MISC_FEATURE
<222> LOCATION: (2)..(2)
<223> OTHER INFORMATION: can be absent or Ile, Leu, Nle, Val, Ala,
      D-Ile, D-Leu, D-Nle, D-Val, D-Ala, or any other hydrophobic amino
      acid
<220> FEATURE:
<221> NAME/KEY: MISC_FEATURE
<222> LOCATION: (3)..(3)
<223> OTHER INFORMATION: Asp, Glu, Lys, or any other amino acid having a
      side chain acid group or amino group
<220> FEATURE:
<221> NAME/KEY: MISC_FEATURE
<222> LOCATION: (3)..(12)
<223> OTHER INFORMATION: The side chain amino or acid group of Xaa3 is
      bonded to the side chain of counter part amino acid Xaa12 to form
      a cyclic peptide
<220> FEATURE:
<221> NAME/KEY: MISC_FEATURE
<222> LOCATION: (4)..(4)
<223> OTHER INFORMATION: can be absent or Ile, Leu, Nle, Val, Ala,
      D-Ile, D-Leu, D-Nle, D-Val, D-Ala, or any other hydrophobic amino
```

```
        acid
<220> FEATURE:
<221> NAME/KEY: MISC_FEATURE
<222> LOCATION: (5)..(5)
<223> OTHER INFORMATION: Arg, Lys, His, Orn,  or any other basic amino
      acids and the terminus is an acid
<220> FEATURE:
<221> NAME/KEY: MISC_FEATURE
<222> LOCATION: (6)..(6)
<223> OTHER INFORMATION: Ile, Leu, Nle, Val, Ala, D-Ile, D-Leu, D-Nle,
      D-Val, D-Ala, or any other hydrophobic amino acid
<220> FEATURE:
<221> NAME/KEY: MISC_FEATURE
<222> LOCATION: (7)..(7)
<223> OTHER INFORMATION: Arg, Lys, His, Orn,  or any other basic amino
      acids and the terminus is an acid
<220> FEATURE:
<221> NAME/KEY: MISC_FEATURE
<222> LOCATION: (8)..(8)
<223> OTHER INFORMATION: can be absent or Arg, Lys, His, Orn,  or any
      other basic amino acids and the terminus is an acid
<220> FEATURE:
<221> NAME/KEY: MISC_FEATURE
<222> LOCATION: (9)..(9)
<223> OTHER INFORMATION: can be absent or Ile, Leu, Nle, Val, Ala,
      D-Ile, D-Leu, D-Nle, D-Val, D-Ala, or any other hydrophobic amino
      acid
<220> FEATURE:
<221> NAME/KEY: MISC_FEATURE
<222> LOCATION: (10)..(10)
<223> OTHER INFORMATION: can be absent or Arg, Lys, His, Orn,  or any
      other basic amino acids and the terminus is an acid
<220> FEATURE:
<221> NAME/KEY: MISC_FEATURE
<222> LOCATION: (11)..(11)
<223> OTHER INFORMATION: Ile, Leu, Nle, Val, Ala, D-Ile, D-Leu, D-Nle,
      D-Val, D-Ala, or any other hydrophobic amino acid
<220> FEATURE:
<221> NAME/KEY: MISC_FEATURE
<222> LOCATION: (12)..(12)
<223> OTHER INFORMATION: Asp, Glu, Lys, or any other amino acid having a
      side chain acid group or amino group
<220> FEATURE:
<221> NAME/KEY: MISC_FEATURE
<222> LOCATION: (13)..(13)
<223> OTHER INFORMATION: Arg, Lys, His, Orn,  or any other basic amino
      acids and the terminus is an acid

<400> SEQUENCE: 49

Xaa Xaa Xaa Xaa Xaa Xaa Xaa Xaa Xaa Xaa Xaa Xaa Xaa
1               5                   10
```